United States Patent

Buysch et al.

[11] Patent Number: 5,824,816
[45] Date of Patent: Oct. 20, 1998

[54] RECOVERY OF CATALYST SYSTEMS FROM DIARYLCARBONATE-CONTAINING REACTION MIXTURES BY MELT CRYSTALLIZATION

[75] Inventors: Hans-Josef Buysch; Carsten Hesse, both of Krefeld; Johann Rechner, Kempen; Hans-Peter Wirges, Krefeld, all of Germany

[73] Assignee: Bayer AG, Leverkusen, Germany

[21] Appl. No.: 825,602

[22] Filed: Apr. 1, 1997

[30] Foreign Application Priority Data

Apr. 9, 1996 [DE] Germany ................ 196 13 973.2

[51] Int. Cl.$^6$ ..................................... C07C 68/00
[52] U.S. Cl. .................... 558/274; 558/271; 558/272; 558/273
[58] Field of Search ................. 558/274, 271, 558/272, 273

[56] References Cited

U.S. PATENT DOCUMENTS 5,239,106 8/1993 Shafer ........................... 558/274
5,495,038 2/1996 Buysch et al. ................... 558/274

FOREIGN PATENT DOCUMENTS 0 218 545    4/1987   European Pat. Off. .
0 521 499    1/1993   European Pat. Off. .
0 687 666   12/1995   European Pat. Off. .

OTHER PUBLICATIONS

Orbit Abstract of EP 0 218 545 (Apr. 15, 1987).
Orbit Abstract of EP 0 521 499 (Jan. 07, 1993).
Orbit Abstract of EP 0 687 666 (Dec. 20, 1995).

*Primary Examiner*—Michael G. Ambrose
*Attorney, Agent, or Firm*—Connolly & Hutz

[57] ABSTRACT

Catalyst systems with a content of a platinum-group-metal catalyst, a co-catalyst, a quaternary salt and a base for the oxidative carbonylation of aromatic hydroxy compounds to the corresponding diaryl carbonates are obtained according to the invention as a residual melt by melt crystallization and can be returned into the carbonylation reaction or worked up to valuable materials. The melt crystallizate, which consists predominantly of diaryl carbonate and the parent aromatic hydroxy compound, is worked up to pure diaryl carbonate and pure hydroxy compound.

9 Claims, No Drawings

RECOVERY OF CATALYST SYSTEMS FROM DIARYLCARBONATE-CONTAINING REACTION MIXTURES BY MELT CRYSTALLIZATION

The present invention relates to a method for recovering catalyst systems from diaryl carbonate-containing reaction mixtures by melt crystallization, wherein a melt crystallizate and a residual melt containing the catalyst system are obtained. The residual melt can be returned into the reactor for producing the diaryl carbonate or worked up to valuable materials. The melt crystallizate is worked up to pure diaryl carbonate and pure hydroxy compound.

U.S. Pat. No. 5,239,106 mentions the separation of diphenyl carbonate from catalyst-containing reaction solutions by crystallizing the 1:1 adduct with phenol, consisting of 30.5 wt % phenol and 69.5 wt % diphenyl carbonate, from reaction mixtures with the aid of suspension crystallization. Disadvantageous with this method is the restriction to a narrow concentration range to enable the 1:1 adduct to be isolated with sufficiently high yield, i.e. diphenyl carbonate concentrations of at least 50 wt % to 70 wt %. In order that the resulting suspensions may still be processable with the aid of filters, at least a two-stage method involving sophisticated equipment is required. Moreover the catalyst system cannot be separated completely by this method, since the filtered-off crystals still possess adhering mother liquor and inclusions of mother liquor. During the subsequent working up of the 1:1 adduct by distillation, these non-separated catalyst components have a negative effect through the catalysis of by-product formation and DPC decomposition. The proposed washing of the crystallizate with a mixture of 9% water and 91% phenol reduces the yield by dissolving large parts of the 1:1 adduct. Moreover this treatment increases the water content of the adduct crystals, which causes DPC losses due to hydrolysis in the subsequent distillation columns, i.e. in those for the DPC isolation and for the separation of water from the washing solution used. Moreover the description of the method of U.S. Pat. No. 5,239,106 is not comprehensible without effort by the individual, since important parameters are not listed there. For example, no details are given of the inoculation system or the nature and amount of the inoculating material, on the type of crystallizer, such as agitated vessel, rotary crystallizer etc., on the agitation system, such as agitator type, agitation geometry, specific agitation rate, on the cooling system, such as cooling rate, starting temperature and final temperature of the cooling process, or on holding times and post-stirring times, for instance at the final cooling temperature.

To permit reaction solutions with a DPC content of less than 50 wt % also to be processed, an enrichment by distillation, with the disadvantages described above of a distillation in the presence of catalyst components, is imperative. In addition a thermal stress of the reaction solution leads to a deactivation of the catalyst system, which requires an expensive fresh feeding of the catalyst components into the process. All these disadvantages described make the method inflexible and unattractive and prevent a technical realization.

EP-A 687 666 describes a method for the purification of diphenyl carbonate by the fractional melt crystallization of highly concentrated reaction mixtures in the temperature range from 45° to 85° C., Diphenyl carbonate purities of 97.5 and 99.5% are obtained. A disadvantage of this method is the restriction to reaction mixtures with a diaryl carbonate content of more than 70 wt.-%. Reaction solutions with diaryl carbonate contents of less than 70 wt.-% cannot be processed by this method. They would have to be concentrated to the required contents, e.g. by distillation. During this thermal stress the catalyst system causes side reactions and is deactivated in the process. Therefore this method is uneconomic and cumbersome for reaction solutions with diphenyl carbonate contents of less than 70 wt.-%.

The object was to find a gentle method for separating and recovering the catalyst systems from diaryl carbonate-containing reaction solutions with different diaryl carbonate contents with high space-time yield, without deactivation of the catalyst system, and under economic, technically realizable and reproducible conditions.

It has now been found that the disadvantages described can be overcome by removing the reaction mixture from the reactor, obtaining a catalyst-containing melt in a fractional melt crystallization process by temperature reduction and inoculation of the reaction solution, separating residues of the catalyst system from the crystallizate by sweating, working up the crystallizates consisting of a mixture of diaryl carbonate and aromatic hydroxy compound into high-purity diaryl carbonate by crystallization or distillation and afterwards returning the reaction solution containing the catalyst system into the reactor. Surprisingly it was found that in the case of the diaryl carbonate/phenol system the composition of the crystallizates varies as a function of the diphenyl carbonate content of the reaction solution. The 1:1 adduct occurred only in a very narrow concentration range. Washing of the crystallizates obtained is not necessary. Moreover no thermal damaging of the catalyst system takes place, thus reducing catalyst deactivation to a minimum. A particular advantage of the method according to the invention consists in the fact that it can be carried out in one stage without a filtration step. Reaction solutions having diaryl carbonate contents of 20 to 70% can be used. In addition, different diaryl carbonates may be contained in the reaction solutions useable.

Consequently the invention relates to a method for recovering catalyst systems containing a platinum-group-metal catalyst, a co-catalyst, a quaternary salt and a base from reaction mixtures for producing diaryl carbonates of formula (I)

R—O—CO—O—R   (I)

by oxidative carbonylation of the aromatic hydroxy compounds of formula (II)

R—O—H   (II)

wherein in the formulae

R denotes substituted or non-substituted $C_6$–$C_{15}$-aryl, preferably substituted or non-substituted phenyl, particularly preferably non-substituted phenyl, and having a diaryl carbonate content of at least 15 and less than 70 wt.-%, relative to the total weight of the reaction mixtures, which is characterised in that a) the reaction mixture is transferred from the reactor for producing the diaryl carbonate into an apparatus suitable for the melt crystallization, b) the melt crystallization is initiated in the suitable apparatus by temperature reduction and inoculation, c) the melt crystallizate, consisting predominantly of diaryl carbonate and the parent aromatic hydroxy compound, is separated from the residual catalyst-containing melt, d) the melt crystallizate is worked up to pure diaryl carbonate and pure aromatic hydroxy compound and
e) the residual catalyst-containing melt is recycled into the reactor for producing diaryl carbonate or worked up in order to obtain valuable materials.

R is $C_6$–$C_{15}$-aryl, such as phenyl, biphenylyl, naphthyl, anthryl or HO—$C_6H_4$—$(C(CH_3)_2)$—$C_6H_4$— (i.e. ROH is bisphenol A), preferably phenyl. The aromatic rings can each be substituted once or twice by —$CH_3$, —$C_2H_5$, —Cl, —Br or —F; particularly preferably R is non-substituted phenyl.

To carry out the method according to the invention, tube bundle crystallizers or modified plate heat exchangers of varying construction with or without partitioning of the melt, with or without application of pulsations and with or without sub-division of the tubes into segments with separate discharge can e.g. be used. Falling-film crystallizers of varying design, e.g. those known from EP-A 218 545, can also be used. Other useable items of equipment are bubble column crystallizers, cylinder and belt crystallizers. All the units have heat exchange surfaces and a coolant circuit; the temperatures given below are those of the coolant running back from the heat exchange surfaces. Further details of a continuously operating, suitable crystallizing apparatus are contained in EP-A 521 499.

According to the invention, tube bundle crystallizers, plate heat exchangers of varying construction with or without recycling of the melt or falling-film crystallizers are preferably employed for the method.

In accordance with the method given above, the crystallizing operation in the method according to the invention can be initiated both by spontaneous nucleation and by a defined supply of seed crystals (inoculation). Preferably the crystal formation is initiated by seeding.

The method according to the invention can be combined with purification methods employing distillation. Thus it is possible, after the application of melt crystallization, to carry out a distillation of diphenyl carbonate. The method according to the invention can also be combined with other simple crystallization methods, for example that described in U.S. Pat. No. 5,239,106.

The following descriptions refer by way of example to diphenyl carbonate (DPC). However, the person skilled in the art can easily adapt the process parameters to account for the physical data of other diaryl carbonates.

In case the method according to the invention is conducted in tube bundle crystallizers or plate heat exchangers, the melt is cooled in the range from 53° to 29° C. with a cooling rate of 20 to 0.1 K/h, preferably 10 to 0.5 K/h. During this cooling period, the crystallizing operation is initiated by a defined supply of seed crystals (inoculation) at an inoculation temperature of 53° to 29° C. The amount of seed crystals used is 0.02 to 1 wt.-% (referred to diphenyl carbonate used). The final cooling temperature is in the range from 20° to 48° C. Optionally, the melt is maintained at this temperature for a holding time of up to 100 minutes prior to the separation of the residual melt. Taking both variants into account, therefore, the holding time is 1 to 5 hours. Thereafter the separation of the residual melt takes place, and the crystallizate is further purified by heating at a heating rate of 20 to 0.1 K/h, preferably 10 to 0.5 K/h, up to a final temperature of 29° to 75° C.

In order to improve the degree of purification, further holding points can optionally serve for the separation of further residual melt portions during this heating phase and impurities molten up to these holding points be removed together with the residual melt. In a further embodiment, the primary residual melt containing the molten residual impurities can be separated during the heating operation, without interruption of the heating, and hence be separated from the pure DPC residual melt obtained at higher temperature after melting of the crystallizate.

The pure melt is worked up to pure diaryl carbonate and pure aromatic hydroxy compound, for example by distillation, solution crystallization, extraction or other known methods. The separated (residual) melt is, together with further melts obtained during the "sweating", returned as a catalyst system into the reactor for producing diaryl carbonate or worked up in order to obtain valuable materials, for instance the platinum-group metal.

The following examples are intended to show clearly the procedure according to the invention without limiting it in any way. The experiments in fractionating melt crystallization were conducted in a statically operated column (diameter: 30 mm; height: 900 mm) as layer crystallization. Tetrabutylammonium bromide (TBAB) is regarded as a main contaminant in the examples. TBAB represents a tracer substance which occurs in the highest concentration in the feed and is most easily measurable as a purification factor in the crystallizate. The reaction mixtures can be obtained by known methods for producing diaryl carbonates, for example according to DE-A 19 605 167. Only the relevant constituents DPC, phenol and TBAB, however, are mentioned in the following examples.

EXAMPLES

As given in the following tables (in Example 1: 106.2 g DPC, 489 g phenol and 4.8 g TBAB), reaction mixtures each with a total of 600 g of DPC, phenol and TBAB were introduced as feed into a tube bundle crystallizer; a quasi-continuous mode of operation was achieved by charging several crystallizers in turn. The temperature was 53° C. at the start; the temperature during the inoculation and hence at the start of the crystallization is given in each case. After a holding time the residual melt ("melt"=mother liquor/moli) was drawn off. Thereafter the melting of the crystallizate was started ("pure melt"); heating rate, heating time and final heating temperature are listed in each case. The part amounts first obtained during the melting were united with the mother liquor (moli). The quantity balances are given. The mother liquor containing the whole catalyst system was used for the production of further reaction mixtures. During repeated recycling of the mother liquor a portion of a few per cent of the recycle flow is removed and replaced. The pure melt was worked up by distillation.

$$*TBAB\ \text{depletion factor} = \frac{\text{mass } TBAB \text{ feed/mass } DPC \text{ feed}}{\text{mass } TBAB \text{ pure melt/mass } DPC \text{ pure melt}}$$

Example 1

DPC conc.=17.7%

| crystallization conditions | | |
|---|---|---|
| crystallization temperature | [°C.] | 29 |
| inoculation temperature | [°C.] | 29 |
| final cooling temperature | [°C.] | 20 |
| cooling rate | [K/h] | 2 |
| cooling time | [h] | 4.5 |
| holding time | [h] | 1 |
| final heating temperature | [°C.] | 34 |

-continued crystallization conditions

| | | |
|---|---|---|
| heating rate | [K/h] | 2 |
| heating time | [h] | 7 |

| mass [g] | DPC [g] | phenol [g] | TBAB [g] | depletion factor TBAB |
|---|---|---|---|---|
| feed | 600 | 106.2 | 489.0 | 4.80 |
| melt (moli) | 471.0 | 78.6 | 387.6 | 4.76 |
| pure melt | 129.0 | 27.6 | 101.4 | 0.04 | 35 |

| | | |
|---|---|---|
| space-time yield | [kg/m³*h] | 3.3 |
| DPC yield | [%] | 26 |

Example 2

DPC conc.=48.2% crystallization conditions

| | | |
|---|---|---|
| crystallization temperature | [°C.] | 44 |
| inoculation temperature | [°C.] | 44 |
| final cooling temperature | [°C.] | 42.5 |
| cooling rate | [K/h] | 0.5 |
| cooling time | [h] | 3 |
| holding time | [h] | 1 |
| final heating temperature | [°C.] | 51.5 |
| heating rate | [K/h] | 2 |
| heating time | [h] | 4.5 |

| mass [g] | DPC [g] | phenol [g] | TBAB [g] | depletion factor TBAB |
|---|---|---|---|---|
| feed | 600.0 | 289.2 | 307.4 | 3.36 |
| melt (moli) | 432.1 | 176.7 | 252.2 | 3.24 |
| pure melt | 167.9 | 112.5 | 55.3 | 0.12 | 11 |

| | | |
|---|---|---|
| space-time yield | [kg/m³*h] | 22 |
| DPC yield | [%] | 38.9 |

Example 3

DPC conc.=69.0% crystallization conditions

| | | |
|---|---|---|
| crystallization temperature | [°C.] | 51.5 |
| inoculation temperature | [°C.] | 51.5 |
| final cooling temperature | [°C.] | 48 |
| cooling rate | [K/h] | 0.5 |
| cooling time | [h] | 7 |
| holding time | [h] | 1 |
| final heating temperature | [°C.] | 74.0 |
| heating rate | [K/h] | 2 |

-continued crystallization conditions

| | | |
|---|---|---|
| heating time | [h] | 13 |

| mass [g] | DPC [g] | phenol [g] | TBAB [g] | depletion factor TBAB |
|---|---|---|---|---|
| feed | 600.0 | 414.0 | 182.64 | 3.36 |
| melt (moli) | 359.6 | 253.0 | 103.44 | 3.18 |
| pure melt | 240.4 | 161.0 | 79.2 | 0.18 | 7.4 |

| | | |
|---|---|---|
| space-time yield | [kg/m³*h] | 18 |
| DPC yield | [%] | 38.9 |

We claim:

1. A method for recovering catalyst systems containing a platinum-group-metal catalyst, a co-catalyst, a quaternary salt, and a base from reaction mixtures for producing diaryl carbonates of formula (I)

$$R-O-CO-O-R \quad (I)$$

by oxidative carbonylation of the parent aromatic hydroxy compounds of formula (II)

$$R-O-H \quad (II)$$

wherein in the formulae

R signifies substituted or non-substituted $C_6$–$C_{15}$-aryl, and having a diaryl carbonate content of at least 15 and less than 70 wt %, relative to the total weight of the reaction mixtures, wherein a) the reaction mixture is transferred from the reactor for producing diaryl carbonate into an apparatus suitable for the-melt crystallization, b) the melt crystallization is initiated in the suitable apparatus by temperature reduction and inoculation, c) the melt crystallizate, which consists predominantly of diaryl carbonate and the parent aromatic hydroxy compound, is separated from the residual catalyst-containing melt, d) the melt crystallizate is worked up to pure diaryl carbonate and pure aromatic hydroxy compound and e) the catalyst-containing residual melt is recycled into the reactor for producing diaryl carbonate or worked up in order to obtain valuable materials.

2. The method of claim 1, wherein the apparatus for the melt crystallization is a tube bundle crystallizer or a plate heat exchanger crystallizer.

3. The method of claim 1, wherein the temperature of the reaction mixture is reduced from a start temperature in the range from 53° to 29° C. with a cooling rate of 20 to 0.1 K/h to an end temperature in the range from 20° to 48° C.

4. The method of claim 1, wherein in step b) the melt crystallization is initiated, by temperature reduction and inoculation with solid diaryl carbonate, solid aromatic hydroxy compound or a mixture of both as seed material.

5. The method of claim 4, wherein melt crystallizate from a previous reaction run is used for the inoculation.

6. The method of claim 4, wherein 0.02 to 1 wt % of inoculation material, referred to diaryl carbonate present in the reaction mixture, is used.

7. The method of claim 1, wherein in step c) the melt is maintained at a constant temperature for one or more holding time(s) of 1 to 5 hours prior to the separation of the residual melt.

8. The method of claim 1, wherein in step d) the melt crystallizate is treated by "sweating" prior to the working up, wherein the temperature is increased at a heating rate of 20 to 0.1 K/h into the range of 29° to 75° C. and further residual melt obtained is separated and united with the residual melt first obtained.

9. The method of claim 8, wherein the melt is maintained at a constant temperature for one or more holding time(s) of 1 to 5 hours in the course of the "sweating".

* * * * *